United States Patent [19]
Nishimuta et al.

[11] Patent Number: 5,593,668
[45] Date of Patent: Jan. 14, 1997

[54] CONTROLLING A PLANT PARASITIC NEMATODE WITH PASTEURIA

[75] Inventors: Koichi Nishimuta, Fukaya; Hiroshi Kawada; Takanori Kasumimoto, both of Tsukuba, all of Japan

[73] Assignee: Nematech Co., Ltd., Kawasaki, Japan

[21] Appl. No.: 377,348

[22] Filed: Jan. 24, 1995

[30] Foreign Application Priority Data

Jan. 26, 1994 [JP] Japan ................................ 6-023512

[51] Int. Cl.⁶ .............................. A01N 63/04; C12N 1/12; C12N 1/20
[52] U.S. Cl. ...................... 424/93.4; 435/252.1
[58] Field of Search ................ 424/93.4; 435/252.1

[56] References Cited

U.S. PATENT DOCUMENTS

| | | | |
|---|---|---|---|
| 5,089,263 | 2/1992 | Spiegel et al. | 424/93.4 |
| 5,094,954 | 3/1992 | Provic et al. | 435/242 |
| 5,248,500 | 9/1993 | Ayanaba | 424/93.4 |

Primary Examiner—Michael G. Wityshyn
Assistant Examiner—Blaine Lankford
Attorney, Agent, or Firm—Oblon, Spivak, McClelland, Maier & Neustadt, P. C.

[57] ABSTRACT

A formulation for controlling a plant parasitic nematode, having Pasteuria spp., as a natural enemy microorganism to the nematode, suspended in water.

10 Claims, No Drawings

CONTROLLING A PLANT PARASITIC NEMATODE WITH PASTEURIA

The present invention relates to a technique for controlling a plant parasitic nematode which damages crop plants, by means of an obligate parasitic natural enemy microorganism.

Heretofore, for the control of a plant parasitic nematode, a method of using a chemical control agent or a field husbandry control method such as crop rotation or cultivation of a resistant variety, has been employed. In recent years, it has been common to employ a chemical control method from the economical reason.

However, it is difficult to control nematodes living in soil, and a large amount of the control agent is required as compared with the control of pests which damage the foliage. Consequently, effects to the environment, such as side effects to the life in soil, pollution of underground water and destruction of the ozone layer, have been worried about.

Whereas, methods for using natural enemies to nematodes are being studied continuously, since the effects will be constant if the conditions are properly controlled, safety to human and animals can be secured, and there will be no adverse effects to the environment.

Among such natural enemies, Pasteuria spp. has been well studied, which is an obligate microparasite to a nematode. To use this microorganism, it has been simple and common to dry and pulverize a plant root containing this microorganism propagated in the bodies of nematodes and apply the pulverized product i.e. dust formulation to soil to control the nematodes, as disclosed, for example, in The American Phytopathological Society Vol. 74, No. 1, 55–60, 1984 and Brazilian Patent No. 9000036.

Further, Japanese Unexamined Patent Publication No. 29506/1987 discloses a suspension concentrate employing this microorganism and a nematocide in combination and its application to the soil surface. However, this is merely one of Formulation Examples intended to demonstrate the effects of the combined use of this microorganism and the nematocide. Namely, there is no disclosure which teaches or suggests that a suspension concentrate is superior to other formulations. Needless to say, there is no disclosure at all about the advanced technology of the suspension concentrate which brings about an increase and stability of the effects of this microorganism.

This microorganism has no mobile ability. Accordingly, to use the above-mentioned dust formulation of the dried plant root containing Pasteuria spp. which is the obligate microparasite to nematodes, it has been important to mix it uniformly in soil so that it is in contact with the nematodes, in order to obtain adequate effects. Further, there has been a problem such that Pasteuria spp. tends to aggregate in the dried plant root or in the formulation, whereby the number of Pasteuria spp. capable of attaching to nematodes decreases substantially.

Therefore, in the control of nematodes in soil, there have been problems such that a large amount of this microorganism which is an obligate microparasite and very poor in the productivity, has to be mixed with soil, pulverization has to be done as far as possible within a range that this microorganism will not be destroyed, whereby the product tends to be expensive as compared with a chemical control agent, and at the time of its application in the field, there has been a problem of scattering due to wind, or a problem that the operator is likely to inhale the dust.

To solve the above problems, the present invention provides:

1. A formulation for controlling a plant parasitic nematode, having Pasteuria spp., as a natural enemy microorganism to the nematode, suspended in water.
2. The formulation for controlling a plant parasitic nematode according to 1, which is heat-treated.
3. The formulation for controlling a plant parasitic nematode according to 1, which contains from 1 to 30% by weight of a non-ionic surfactant.
4. The formulation for controlling a plant parasitic nematode according to 1, wherein Pasteuria spp. is suspended in water at a concentration within a range of from $1 \times 10^5$ spores/ml to $5 \times 10^9$ spores/ml.
5. A method for controlling a plant parasitic nematode, which comprises applying Pasteuria spp., as a natural enemy microorganism to the nematode, to an agricultural field in a form of an aqueous suspension having Pasteuria spp. suspended in water or an aqueous mixture having water added to Pasteuria spp.
6. The method for controlling a plant parasitic nematode according to 5, wherein the concentration of Pasteuria spp. in the aqueous suspension or in the aqueous mixture is within a range of from $1 \times 10^5$ spores/ml to $5 \times 10^9$ spores/ml.

Namely, to disperse this microorganism uniformly to an agricultural field, the plant root containing this microorganism is pulverized and sieved without the conventional drying step, and the obtained product is suspended in water and applied to the field, or the product is suspended in irrigated water to let it penetrate in soil, whereby this microorganism can be effectively attached to the objective plant parasitic nematode with a less number of this microorganism as compared with the conventional plant root powder containing this microorganism or a dust formulation obtained by diluting the conventional plant root powder. In this case, pulverization of the raw plant root is advantageous over pulverization of the dried root, since it can be readily carried out without a worry about physical destruction of this microorganism or death of the microorganism due to heat generated during the pulverization.

The pulverized plant root containing the microorganism which is parasitic on a nematode, may be used as it is or may be sieved or subjected to centrifugal separation to readily concentrate the microorganism. The pulverized product containing this microorganism may be formulated as it is or after application of heat treatment, or by an addition of e.g. a surfactant for promoting the dispersion, into an aqueous suspension concentrate.

The aqueous suspension concentrate can be prepared easily and inexpensively without necessity of a step of drying the pulverized product. However, it is likely that by the propagation of co-existing microorganisms other than this microorganism, a bad odor will be generated, or this microorganism will gradually be decomposed.

In such a case, it will be necessary to add a bactericide or a bacteriostatic agent which is free from affecting this microorganism. However, it is also possible to control the propagation of other microorganisms without affecting the present microorganism by heat treatment e.g. at 65° C. for 30 minutes, and yet in this case, it is possible to maintain the desired properties as an aqueous suspension concentrate.

Further, the added surfactant serves to prevent aggregation of the present microorganism and facilitate redispersion and at the same time is effective for controlling the propagation of other microorganisms. Especially, a non-ionic surfactant is excellent without affecting the present microorganism. The surfactant is used usually at a concentration of from 1 to 30% by weight, preferably from 5 to 20% by weight.

Specific examples of the non-ionic surfactant include a polyoxyethylene alkyl ether, a polyoxyethylene alkylallyl ether, a sorbitan fatty acid ester, a polyoxyethylene sorbitan fatty acid ester, a glycerol fatty acid ester, a polyoxyethylene fatty acid ester, and a polyalkyl glycol.

There is no particular restriction as to the concentration of the present microorganism in the aqueous suspension concentrate of the present invention. However, Pasteuria spp. is suspended in water usually at a concentration within a range of from $1 \times 10^5$ spores/ml to $5 \times 10^9$ spores/ml, preferably from $2 \times 10^7$ spores/ml to $2 \times 10^9$ spores/ml.

Now, the present invention will be described in detail with reference to Examples. However, it should be understood that the present invention is by no means restricted to such specific Examples.

EXAMPLE 1 Effects of suspension concentrate

A tomato root parasitized by a sweet potato root-knot nematode which contained Pasteuria spp. as the present microorganism, was dried, pulverized and sieved to at most 300 μm to obtain a dust formulation. The content of the present microorganism in the dust formulation was $1.0 \times 10^8$ spores/g.

On the other hand, to a raw tomato root containing the present microorganism, twice by weight of water was added, and the mixture was pulverized by a homogenizer for 5 minutes. The pulverized mixture was filtered to at most 100 μm to obtain a suspension, which was centrifugally separated at 3,000 rpm for 30 minutes to obtain a precipitate, which was diluted with water to adjust the concentration to $1.0 \times 10^8$ spores/ml and $1.0 \times 10^6$ spores/ml.

1 g of the dust formulation or 1 ml of the suspension of high concentration was added and mixed to 1 l of soil infested with the treat potato root-knot nematode, and the mixture was filled in a 1/10,000 a pot. The suspension of low concentration was irrigated in an amount of 100 ml from the top of a pot filled with 1 l of soil infested with the nematode. Each pot was maintained at 25° C. for 7 days. Then, the nematodes were separated by Bellman method, and the number of nematodes, the number of attachment, and the attachment ratio were investigated.

The Bellmann method was carried out three times for each pot, whereby separation was carried out at 25° C. for 48 hours using 20 g of the soil. For the number of attachment and the attachment ratio, 100 nematodes were investigated. The results are shown in Table 1.

TABLE 1

| Type of formulation | Number of nematodes | Number of attachment (Number of spores per nematode) | Attachment ratio (%) |
|---|---|---|---|
| Dust formulation mixed | 270 ± 54 | 0.30 ± 0.62 | 9 |
| Suspension mixed | 234 ± 37 | 1.26 ± 2.36 | 42 |
| Suspension irrigated | 180 ± 24 | 2.12 ± 3.60 | 71 |

EXAMPLE 2 Effects of surfactant

Various surfactants and predetermined amounts of water were added to suspension concentrates containing $1 \times 10^9$ spores/ml of the present microorganism to obtain the respective suspension concentrates having a concentration of $5 \times 10^8$ spores/ml, which were stored at 40° C. Each suspension concentrate after storage, was diluted with water to a suspension with a concentration of $5 \times 10^5$ spores/ml. To 50 ml of this diluted suspension, 50 ml of a suspension containing 2,000 sweat potato root-knot nematodes/ml was added, and the mixture was subjected to centrifugal separation at 3,000 rpm for 5 minutes to attach the present microorganism to the nematodes. 30 ml of the suspension of nematodes having the present microorganism attached thereto, was irrigated to tomato seedlings (prits) of 6-leaf stage grown in a 1/10,000a Wagner pot and cultivated at 25° C. for 8 weeks. The root was recovered, and the present microorganism was recovered and the amount of its production was investigated in the same manner as in Example 1. The average value of three tests for each pot is shown in Table 2.

TABLE 2

| | | Productivity of microorganism | |
|---|---|---|---|
| Surfactant | Concentration % | 40° C. for 1 month ×10⁸ spores/pot | 40° C. for 2 months ×10⁸ spores/pot |
| Tween-20 | 10 | 7.5 ± 1.2 | 7.2 ± 1.7 |
| Tween-20 | 30 | 4.4 ± 1.7 | 3.4 ± 0.9 |
| Tween-20 | 50 | 0.1 ± 0.1 | 0.0 ± 0.0 |
| Emulgen-913 | 10 | 7.7 ± 1.2 | 8.2 ± 0.8 |
| Poise-532A | 10 | 7.7 ± 1.1 | 0.2 ± 0.1 |
| Aerol-CT-1 | 10 | 0.1 ± 0.1 | 0.0 ± 0.0 |

Tween-20: Polyoxyethylenesorbitan monolaurate
Emulgen-913: Polyoxyethylenenonylphenyl ether
Poise-532A: Polycarboxylic acid
Aerol-CT-1: Dialkyl sulfosuccinate EXAMPLE 3 Survival of microorganisms by heat treatment A suspension concentrate containing $5 \times 10^{8}$/g of the microorganism was treated at each temperature for 30 minutes, and the autoclave treatment was conducted at 115° C. for 15 minutes. Then, the microorganism was attached to nematodes, and the amount of the production of the microorganism was investigated in the same manner as in Example 2. The average value of three tests for each case is shown in Table 3.

TABLE 3

| Temp. °C. | Treating time min. | Productivity of microorganism ×10⁸ spores/pot | Formulation of fungi |
|---|---|---|---|
| 55 | 30 | 7.7 ± 0.8 | Nil |
| 65 | 30 | 8.2 ± 1.3 | Nil |
| 75 | 30 | 7.2 ± 1.6 | Nil |
| 115 | 15 | 0.0 ± 0.0 | Nil |
| Control 4 | — | 7.5 ± 0.8 | Substantial |

EXAMPLE 4 Difference in suspensibility depending upon the type of formulation

A tomato root containing the microorganism was added to water, pulverized, filtered and centrifugally separated, in the same manner as in Example 1. ① Water was added to the centrifugally separated product to adjust the concentration of the microorganism to $1 \times 10^9$ spores/g (hereinafter referred to as an aqueous suspension concentrate). ② Emulgen-913 was added in an amount of 10% by weight to the centrifugally separated product, and then water was added to adjust the concentration of the microorganism to $1 \times 10^9$ spores/g (hereinafter referred to as an active suspension concentrate). ③ The same amount of the tomato root as used in ① or ②, was dried (water content: 11%) and pulverized to obtain a dust formulation adjusted to have a particle size of at most 300 μm (hereinafter referred to as a dust formulation). Immediately after the preparation of the above three formulations, they were left to stand at 40° C. for 2 months. Then, 1 g of each was sampled into a cylinder for testing suspensibility, and water was added thereto to bring the volume to 100 ml. The cylinder was repeatedly gently turned over 30 times and left to stand still for 60 minutes. Water was sampled from the middle layer of the cylinder, and the microorganism per volume was quantitatively analyzed. The average value of three tests for each formulation is shown in Table 4.

TABLE 4

| Type of formulation | At the time of preparation ×10⁷ spores/ml | After 2 month at 40° C. ×10⁷ spores/ml |
| --- | --- | --- |
| Aqueous suspension concentrate | 0.82 ± 0.12 | 0.58 ± 0.18 |
| Active suspension concentrate | 0.95 ± 0.23 | 1.04 ± 0.25 |
| Dust formulation | 0.17 ± 0.06 | 0.10 ± 0.03 |

We claim:

1. An aqueous-suspended composition for controlling a plant parasitic nematode, which comprises, in water:
   a) an effective amount of a species of Pasteuria which is parasitic to a plant parasitic nematode; and
   b) about 1 to 30% by weight of a surfactant effective to facilitate redispersion and to control propagation of other microorganisms, said surfactant being selected from the group consisting of polyoxyethylene alkyl ether, polyoxyethylene alkylallyl ether, sorbitan fatty acid ester, polyoxyethylene sorbitan fatty acid ester, glycerol fatty acid ester, polyoxyethylene fatty acid ester and polyalkyl glycol.

2. The composition of claim 1, which is heat-treated to control propagation of other microorganisms without affecting the species of Pasteuria.

3. The composition of claim 1, wherein said surfactant is used in the amount of from about 5 to 20% by weight.

4. The composition of claim 1, wherein said species of Pasteuria is suspended in water at a concentration within a range of from about $1 \times 10^5$ spores/ml to $5 \times 10^9$ spores/ml.

5. The composition of claim 4, wherein said species of Pasteuria are suspended in water at a concentration within a range of from about $2 \times 10^7$ spores/ml to $2 \times 10^9$ spores/ml.

6. A method for controlling a plant parasitic nematode, which comprises applying to an agricultural field, an aqueous-suspended composition, which comprises, in water:
   a) an effective amount of a species of Pasteuria which is parasitic to a plant parasitic nematode; and
   b) about 1 to 30% by weight of a surfactant effective to facilitate redispersion and to control propagation of other microorganisms, said surfactant being selected from the gorup consisting of polyoxyethylene alkyl ether, polyoxyethylene alkylallyl ether, sorbitan fatty acid ester, polyoxyethylene sorbitan fatty acid ester, glycerol fatty acid ester, polyoxyethylene fatty acid ester and polyalkyl glycol.

7. The method of claim 6, wherein said composition is heat-treated to control propagation of other microorganisms without affecting the species of Pasteuria.

8. The method of claim 6, wherein said species of Pasteuria in said composition are suspended in water at a concentration within a range of from about $1 \times 10^5$ spores/ml to $5 \times 10^9$ spores/ml.

9. The method of claim 6, wherein said surfactant is used in the amount of from about 5 to 20% by weight.

10. The method of claim 6, wherein said species of Pasteuria is suspended in water at a concentration within a range of from about $2 \times 10^7$ spores/ml to $2 \times 10^9$ spores/ml.

\* \* \* \* \*